United States Patent [19]

Testerman

[11] Patent Number: 5,540,732
[45] Date of Patent: *Jul. 30, 1996

[54] METHOD AND APPARATUS FOR IMPEDANCE DETECTING AND TREATING OBSTRUCTIVE AIRWAY DISORDERS

[75] Inventor: Roy L. Testerman, New Hope, Minn.

[73] Assignee: Medtronic, Inc., Minneapolis, Minn.

[ * ] Notice: The term of this patent shall not extend beyond the expiration date of Pat. No. 5,540731.

[21] Appl. No.: 310,120

[22] Filed: Sep. 21, 1994

[51] Int. Cl.⁶ .................................................. A61N 1/36
[52] U.S. Cl. ................................................................ 607/42
[58] Field of Search .................................. 607/42, 46, 48; 128/716

[56] References Cited

U.S. PATENT DOCUMENTS

| | | |
|---|---|---|
| 3,608,542 | 9/1971 | Pacela et al. . |
| 3,942,513 | 3/1976 | Frank . |
| 3,950,799 | 4/1976 | Frank . |
| 4,289,142 | 9/1981 | Kearns . |
| 4,387,722 | 6/1983 | Kearns . |
| 4,422,458 | 12/1983 | Kravath . |
| 4,596,251 | 6/1986 | Plicchi et al. . |
| 4,648,407 | 3/1987 | Sackner . |
| 4,757,824 | 7/1988 | Chaumet . |
| 4,803,997 | 2/1989 | Bowman . |
| 4,827,935 | 5/1989 | Geddes et al. . |
| 4,830,008 | 5/1989 | Meer . |
| 4,870,578 | 9/1989 | Vysin et al. . |
| 4,999,772 | 3/1991 | Bowman et al. . |
| 5,123,425 | 6/1992 | Shannon, Jr. et al. . |
| 5,131,399 | 7/1992 | Sciarra . |
| 5,174,287 | 12/1992 | Kallok et al. . |
| 5,178,156 | 1/1993 | Takishima et al. . |
| 5,190,053 | 3/1993 | Meer . |
| 5,201,808 | 4/1993 | Steinhaus et al. . |
| 5,206,807 | 4/1993 | Hatke et al. . |
| 5,211,173 | 5/1993 | Kallok et al. . |
| 5,215,082 | 6/1993 | Kallok et al. . |
| 5,271,395 | 12/1993 | Wahlstrand et al. . |
| 5,329,932 | 7/1994 | Yount . |
| 5,335,657 | 8/1994 | Terry, Jr. et al. . |
| 5,335,666 | 8/1994 | Bowman et al. . |

OTHER PUBLICATIONS

"Laryngeal Pacemaker. II. Electronic Pacing of Reinnervated Posterior Cricoartyenoid Muscles in the Canine", Broniatowski, M. et al. Laryngoscope 95, 1985:1194–98.

"Diaphragm Pacing: Present Status", Glenn, Pace, vol. I, 1978:357–370.

"Abstract —Idiopathic Hypersomnia Revisited: The Unknown Upper Airway Resistance Syndrome", Sleep Res., vol. 20, 1991:251.

Primary Examiner—William E. Kamm
Attorney, Agent, or Firm—Daniel W. Latham; Harold R. Patton

[57] ABSTRACT

A method for treating upper respiratory obstructions in a patient by electrical stimulation of muscles of the upper airway including surgically implanting a impedance sensing circuit into the patient such that the impedance sensor is capable of providing a signal characteristic of transthoracic impedance in the patient. The implanted impedance sensing circuit allows the inspiratory phase of the patient's respiratory cycle to be identified and electrical stimulation to be reliably applied during the inspiration phase.

12 Claims, 8 Drawing Sheets

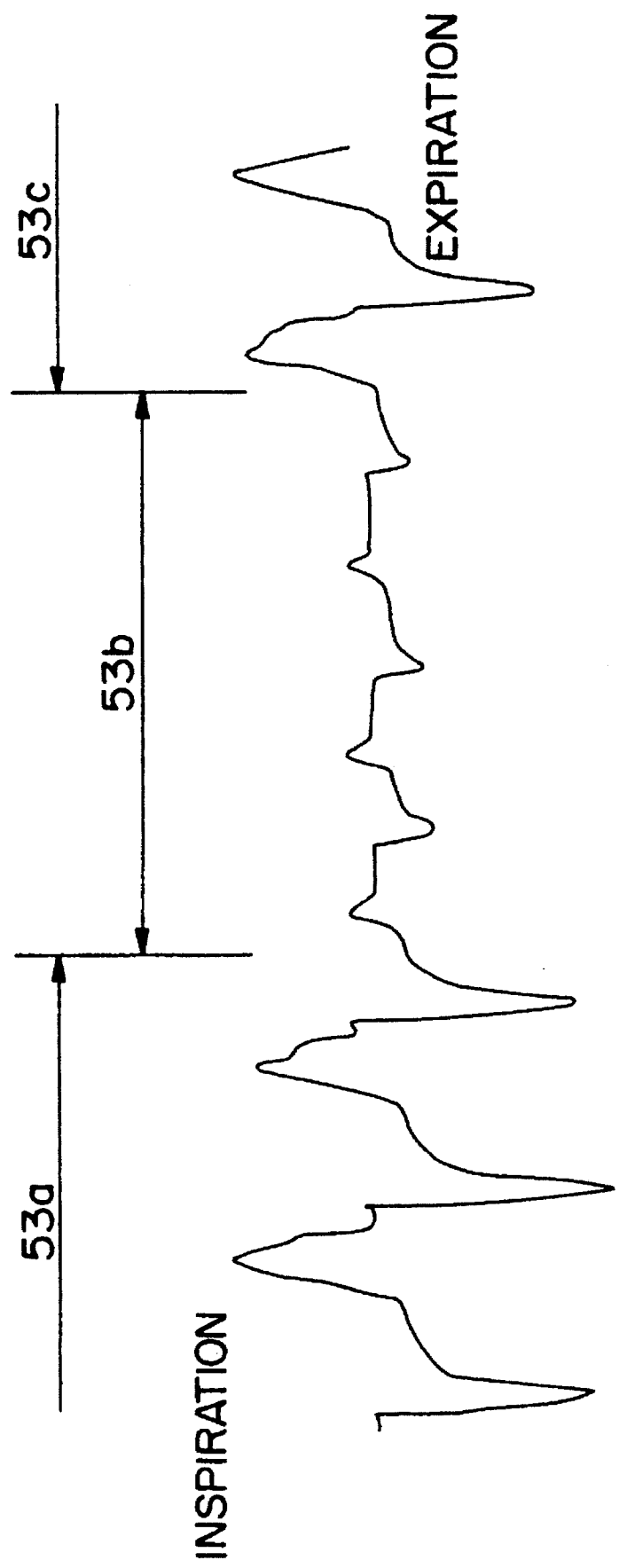

METHOD AND APPARATUS FOR IMPEDANCE DETECTING AND TREATING OBSTRUCTIVE AIRWAY DISORDERS

BACKGROUND OF THE INVENTION

The present invention relates to medical devices which employ electrical stimulation in the treatment of obstructive airway disorders such as obstructive sleep apnea or upper airway resistance syndrome.

Sleep apnea has been known for some time as a medical syndrome in two generally recognized forms. The first is central sleep apnea, which is associated with the failure of the body to automatically generate the neuro-muscular stimulation necessary to initiate and control a respiratory cycle at the proper time. Work associated with employing electrical stimulation to treat this condition is discussed in Glenn, "Diaphragm Pacing: Present Status", Pace, V. I, pp 357–370 (July-September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to their collapse (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the muscle dilator. The muscle dilators are intimately linked to the respiratory muscles and these muscles respond in a similar manner to a stimulation or a depression of the respiratory center. The ventilatory fluctuations observed during sleep (alternately enhancement and depression of periodic respiration) thus favors an instability of the superior airways and the occurrence of oropharyngeal obstruction. The respiratory activation of the genioglossus has been particularly noted to be ineffective during sleep. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The electroencephalographic awakening which precedes the easing of obstruction of the upper airways is responsible for the fragmentation of sleep. The syndrome is therefore associated with an increased morbidity (the consequence of diurnal hypersomnolence and cardiovascular complications). Other conditions affecting the upper airway are also known such as upper airway resistance syndrome as described in Guilleminault, C, et al, Idiopathic Hypersomnia Revisited: The Unknown Upper Airway Resistance Syndrome, Sleep Res 20: 251, 1991 which is hereby incorporated herein by reference or vocal cord paralysis as set forth in Broniatowsld, M. et al., Laryngeal Pacemaker. II. Electronic Pacing of Reinnervated Posterior Cricoarytenoid Muscles in the Canine, Laryngoscope 95: 1194–98, 1985 which is hereby incorporated herein by reference.

A method for treatment of obstructive sleep-apnea syndrome and other upper airway conditions is to generate electrical signals to stimulate those nerves which activate the patient's upper airway muscles in order to maintain upper airway patency. For example, in U.S. Pat. No. 4,830,008 to Meer, inspiratory effort is monitored and electrical signals are directed to upper airway muscles in response to the monitored inspiratory effort. Or, in U.S. Pat. No. 5,123,425 a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. Or in U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of obstructive sleep apnea is assumed and electrical stimulation is applied to the musculature of the upper airway. Or, in U.S. Pat. No. 5,178,156 issued to Wataru et al, respiration sensing includes sensors for sensing breathing through left and right nostrils and through the mouth which identifies an apnea event and thereby triggers electrical stimulation of the genioglossus. Or, in U.S. Pat. No. 5,190,053 issued to Meer, an intra-oral, sublingual electrode is used for the electrical stimulation of the genioglossus to maintain the patency of an upper airway. Or in U.S. Pat. No. 5,211,173 issued to Kallok et al, sensors are used to determine the effectiveness of the stimulation of the upper airway and the amplitude and pulse width of the stimulation are modified in response to the measurements from the sensors. Or in U.S. Pat. No. 5,215,082 issued to Kallok et al, upon sensing of the onset of an apnea event, a stimulation generator provides a signal for stimulating the muscles of the upper airway at a varying intensity such that the intensity is gradually increased during the course of the stimulation. However, even with these modes of therapy there remain many practical difficulties for implementing them in a medically useful treatment system. In particular, if stimulation occurs in response to detected inspiration or to misdetected apnea events, the stimulation may make it difficult for the patient to get to sleep initially or to return to sleep after awakening. According to the Meer '008 patent, the solution to this problem is to monitor the action potentials of the upper airway muscles to determine when the patent is awake and to commence stimulation only when normal upper airway muscle activity is not detected. However, this approach presents many practical difficulties in implementation and can lead to inappropriate stimulation or failure to stimulate reliably.

It is therefore an object of the invention to provide an apnea treatment device and method which includes practical detection of respiratory effort and treatment in response to the detected respiratory effort.

SUMMARY OF THE INVENTION

A method for treating obstructive upper airway conditions in a patient by electrical stimulation of muscles of the upper airway includes detecting inspiratory effort and then stimulating muscles of the upper airway in response to the inspiratory effort. Such a device can be implemented in a fully implantable stimulation system. An implantable pulse generator (IPG) such as a Medtronic ITREL II Model 7424 modified to include an input from a respiratory sensor can be implanted in a patient. The Medtronic ITREL II IPG has advanced programmable features permitting mode changes by transcutaneous RF telemetry. The patient-controllable parameters of the device's operation can therefore be controlled by the patient through a small, hand-held telemetry device while the physician can preset additional operational parameters of the device through an external programmer.

Of critical importance in such a system is the type and location of a respiratory sensor that will allow the device to detect and analyze the respiratory effort of the patient. It has been found that an impedance sensor such as those used in measuring minute volume for control of output rate of heart pacemakers can be used to provide a respiratory effort sensor. Such sensors are disclosed in U.S. Pat. No. 5,201,808 issued to Steinhaus, et. al. or U.S. Pat. No. 5,271,395 issued to Wahlstrand, et. at. or U.S. Pat. No. 4,596,251 issued to Plicchi, et. al., all of which are hereby incorporated herein by reference in their entirety. The impedance sensor is surgically implanted at the time of implantation of the IPG.

In order to detect respiratory effort, the electrical impedance time variation of a part of the chest is determined by means of two implanted electrodes. For example, the electrodes may be subcutaneously positioned, or they may be placed on the IPG case and separated by an electrically insulating part on the same case. Therefore, one electrode can be placed in any suitable and non-critical position vis-a-vis the second electrode keeping in mind that such position has to allow the detection of geometric variations of a part of the chest barely affected by the movements of the upper limbs of the patient. In a preferred embodiment, one electrode is the housing of the case and the second electrode is a ring electrode about the lead extending to the nerve electrode assembly. To measure impedance, a current is forced between the IPG's conductive housing and the ring electrode of the stimulation lead, and the resultant voltage is measured. Additional filtering of the impedance signal may also be required in order to remove physiological artifacts such as movement artifacts. Inspiration-synchronous stimulation is then provided from the pulse generator through a lead to an electrode around a nerve.

A medical device which includes such pressure sensing for treatment of airway conditions can be made according to the detailed description which follows.

BRIEF DESCRIPTION OF THE DRAWINGS

FIG. 2a shows a respiratory effort waveform and indicated phases of the respiratory effort waveform. FIG. 2b shows a graph of a respiratory airflow waveform with FIG. 2c showing the corresponding respiratory effort waveform.

FIG. 4c is a respiratory waveform showing respiratory airflow (as opposed to the respiratory effort waveform shown in FIGS. 4a and 4b) in a patient during an apnea event.

DETAILED DESCRIPTION OF THE PREFERRED EMBODIMENTS

Figure 1:
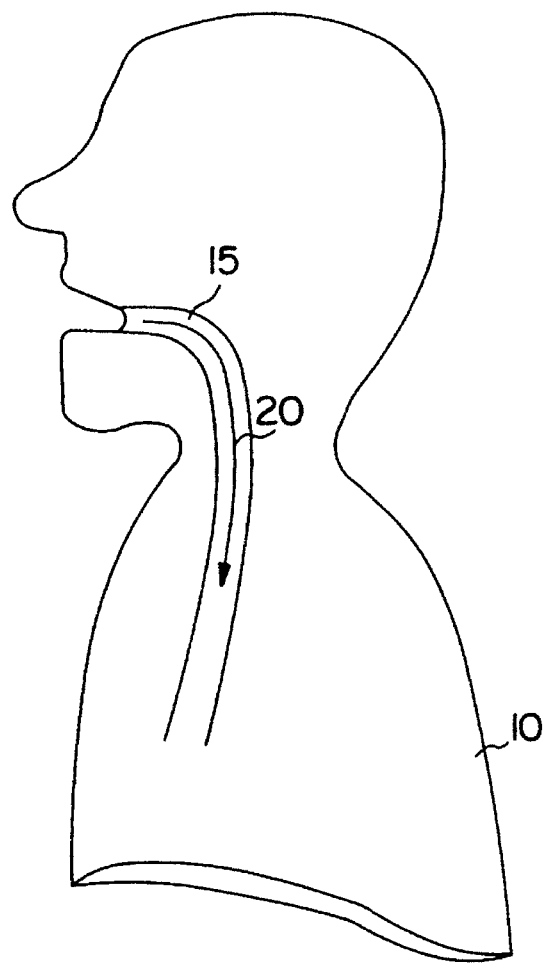
FIG. 1 is a side sectional diagram of a patient having normal respiratory activity.
Figure 2A:
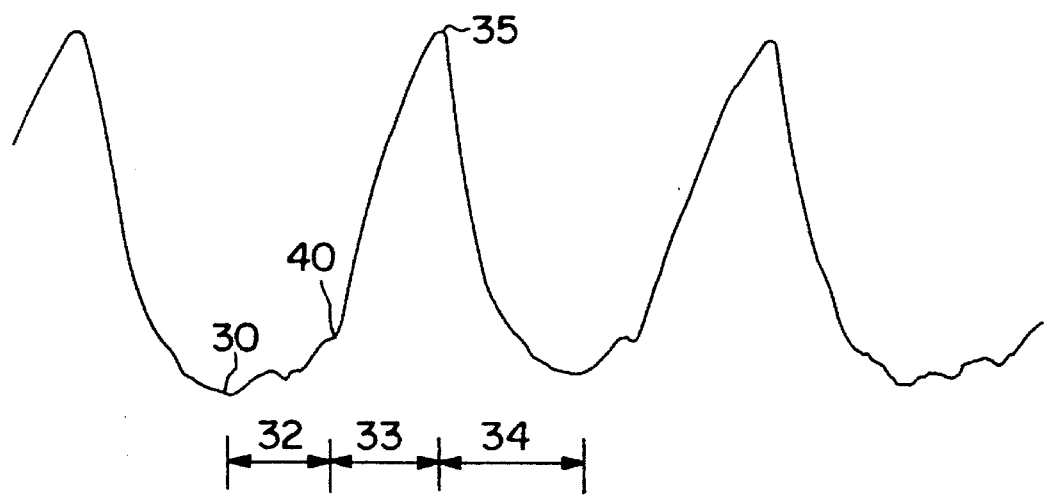
FIGS. 2a–c are graphs of normal respiratory waveforms (shown with full normal inspiration at the peak).
Figure 2B:
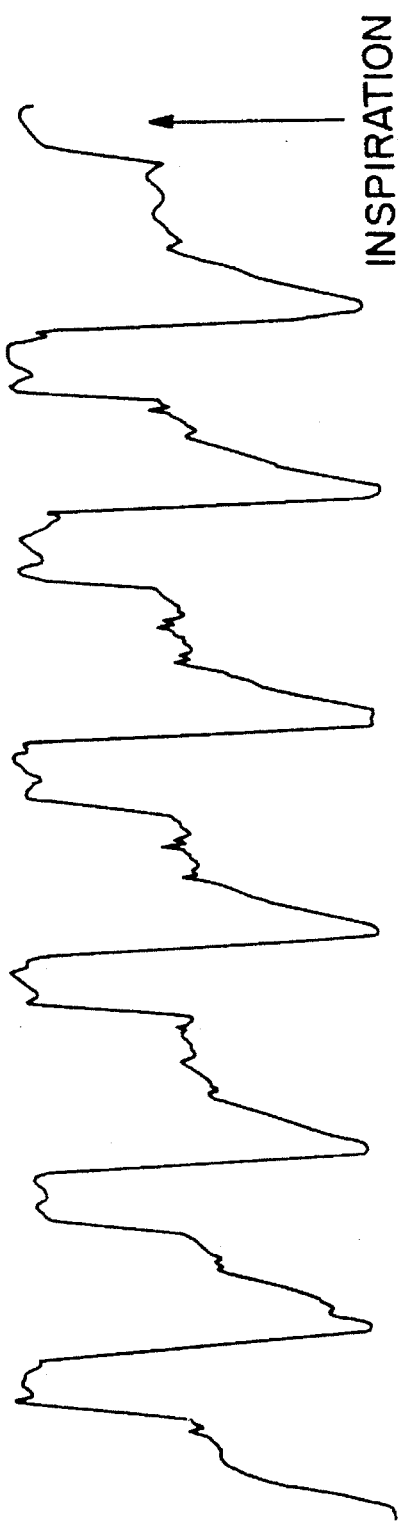
Figure 2C:
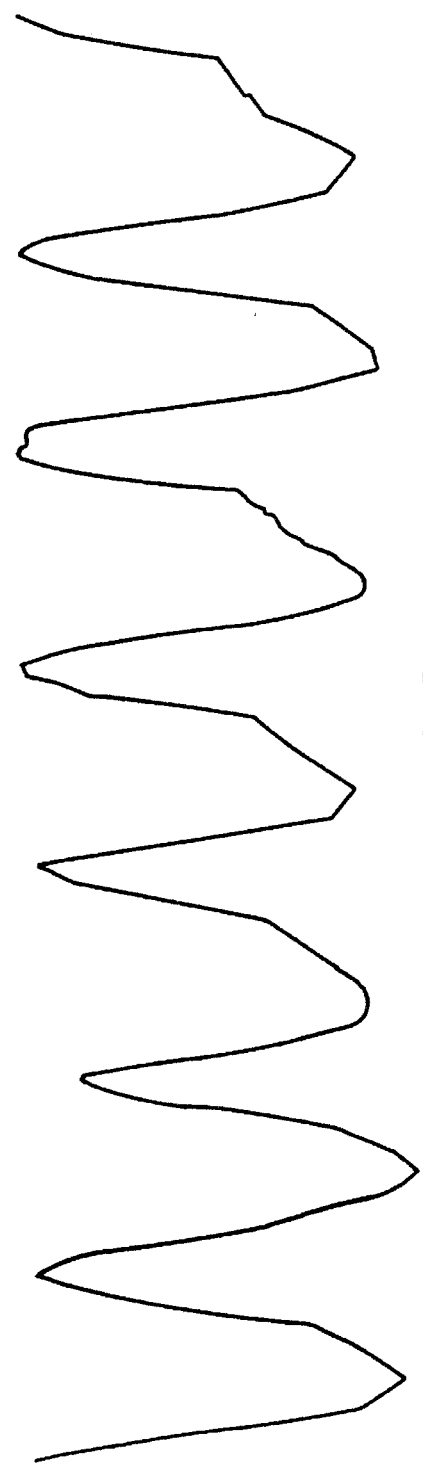

The present invention relates to an apparatus and method for treatment of obstructive diseases of the upper airway by administering stimulation of the musculature of the upper airway in synchrony with the inspiratory phase of the respiratory cycle. In FIGS. 1 and 2a–c, normal respiratory activity is depicted. In FIG. 1, a patient 10 has an airway 15 which is remains patent during inspiration of air 20. FIG. 2a shows a typical respiratory effort waveform for two complete respiratory cycles. Each wave of the waveform is characterized by a negative peak 30 on completion of expiration, a positive peak 35 on completion of inspiration and a turning point 40 which indicates the onset of inspiration. Each wave of the waveform can therefore be separated into a period of respiratory pause 32, an inspiratory phase 33 and an expiratory phase 34. Other characteristics of the waveform could also be identified in connection with tracking and analyzing the respiratory waveform to monitor respiratory activity in upper airway stimulation treatment. In normal respiration, the respiratory effort waveform is related to airflow as set forth in FIGS. 2b and 2c. In FIG. 2b a trace of normal respiratory airflow from a flow transducer is shown while FIG. 2c shows the corresponding trace of the normal respiratory effort which produces the airflow.

Figure 3:
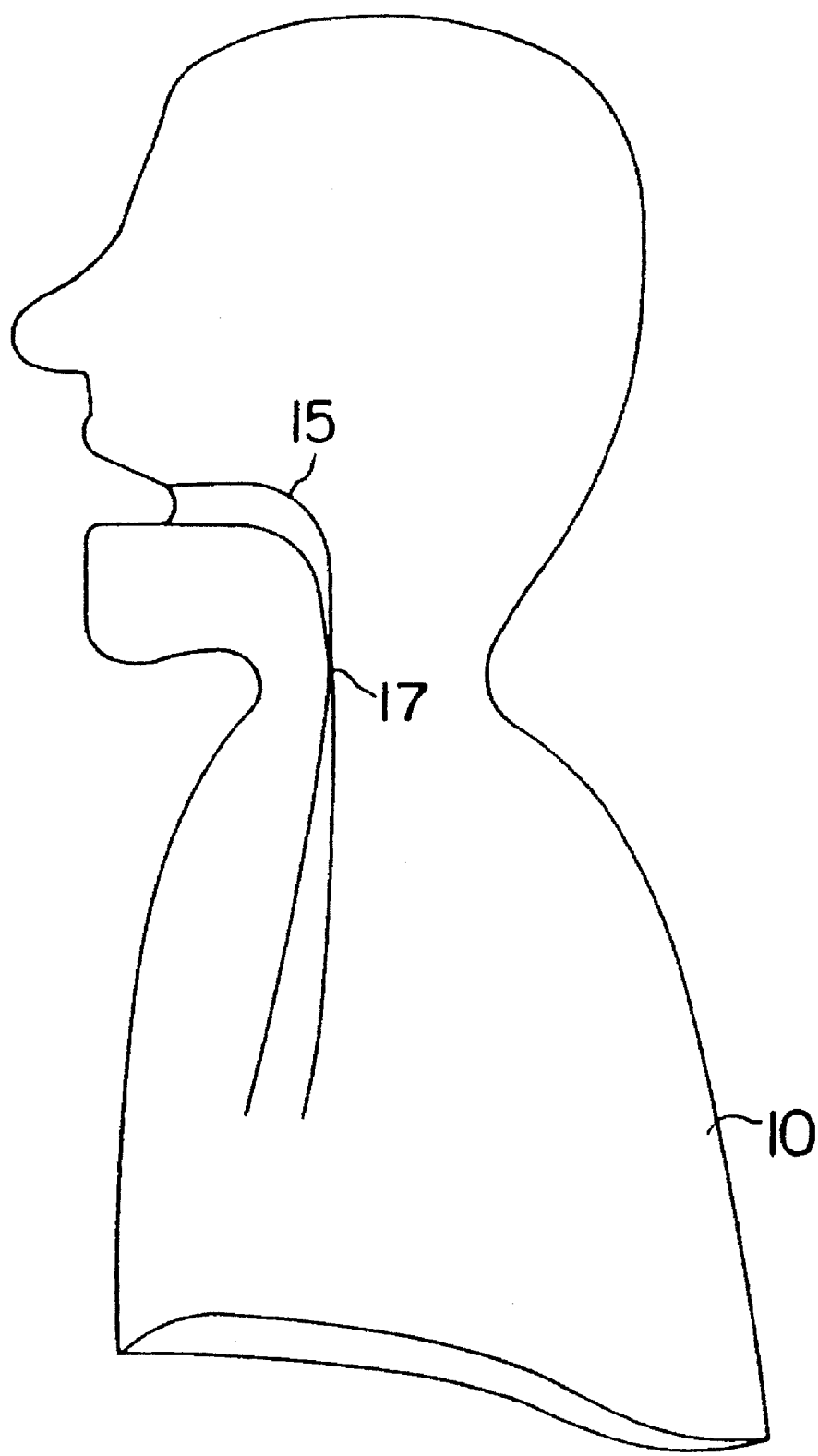
FIG. 3 is a side sectional diagram of the patient of FIG. 1 at the onset of to obstructive apnea.
Figure 4A:
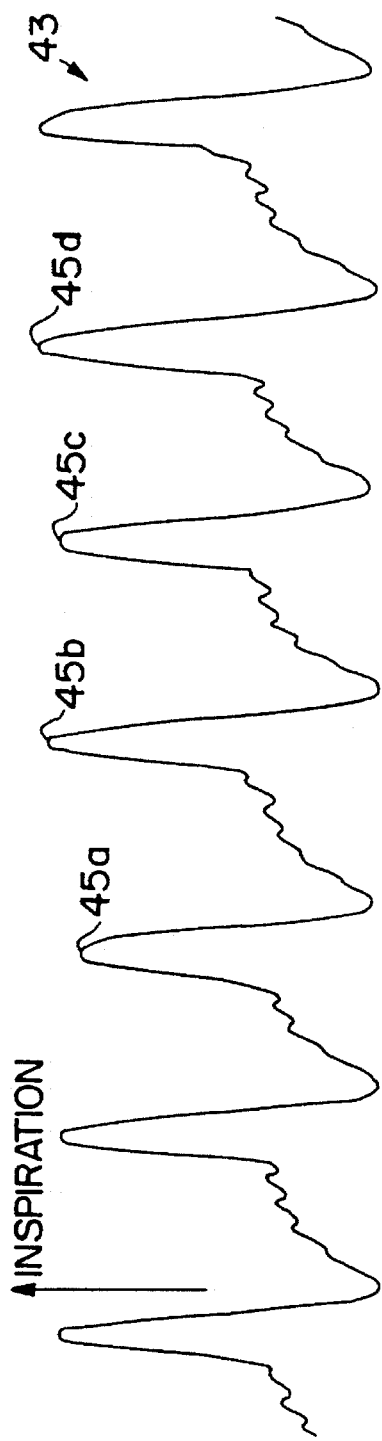
FIGS. 4a and 4b are respiratory waveforms of inspiratory effort showing normal inspiratory effort (FIG. 4a) and the change in normal inspiratory effort at the onset of an apnea event (FIG. 4b).
Figure 4B:
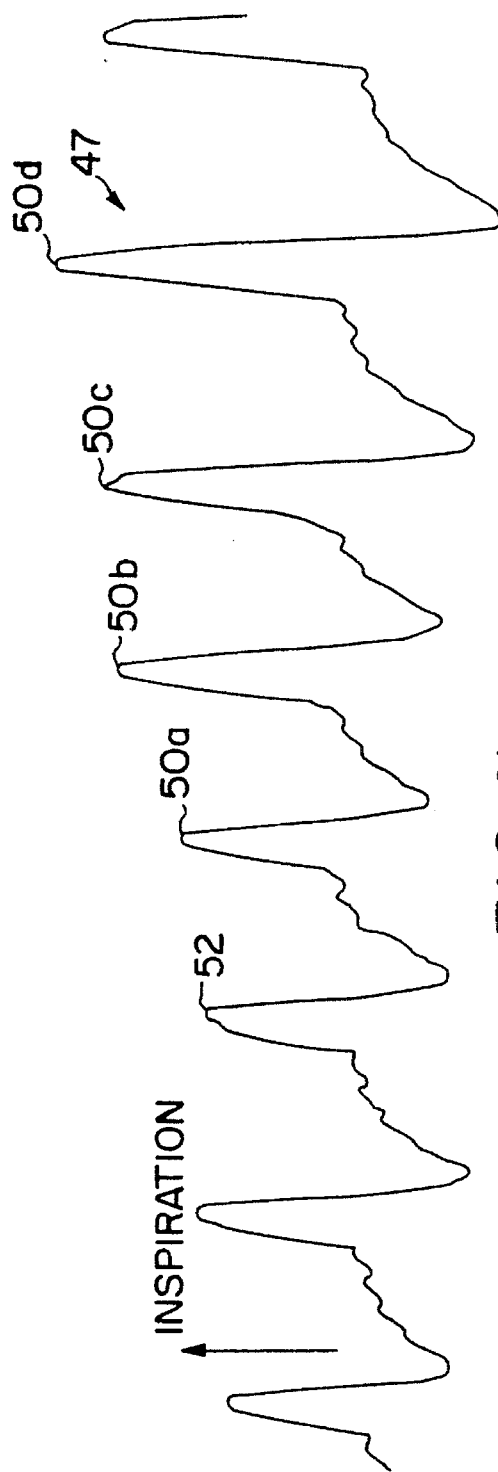

In FIGS. 3 and 4b, respiration in the same patient at the onset of an obstructive sleep apnea event is depicted. FIG. 3 shows the patient 10 and airway 15 with an airway obstruction 17 that is characteristic of an obstructive apnea event. FIG. 4a shows that in a normal respiratory effort waveform 43, the inspiratory peaks 45a–d are of approximately the same amplitude. By comparison in FIG. 4b, in a waveform 47 the inspiratory peaks 50a–d become significantly greater in amplitude at the onset of obstructive apnea than the immediately preceding inspiratory peak 52. This is reflective of the increased inspiratory effort undertaken by the patient in response to the difficulty of breathing through the obstructed airway.

In the device and method of the present invention, the increased respiratory effort is avoided by synchronized stimulation of one or more muscles in the upper airway which hold the airway open during the inspiratory phase. The muscle or muscles stimulated can be selected from any number of muscles of the upper airway such as the genioglossus muscle which may be stimulated by a cuff electrode placed around the hypoglossal nerve. The effect of this stimulation on obstructive sleep apnea can be seen in the airflow trace of FIG. 4c. During a first period indicated as 53a, stimulation is enabled, thereby producing a normal respiratory airflow. During a second period indicated as 53b, stimulation is disabled causing obstruction of the airway and reduction in airflow volume (apnea). During a third period indicated as 53c, stimulation is resumed, restoring patency to the airway and increasing airflow volume.

Figure 5:
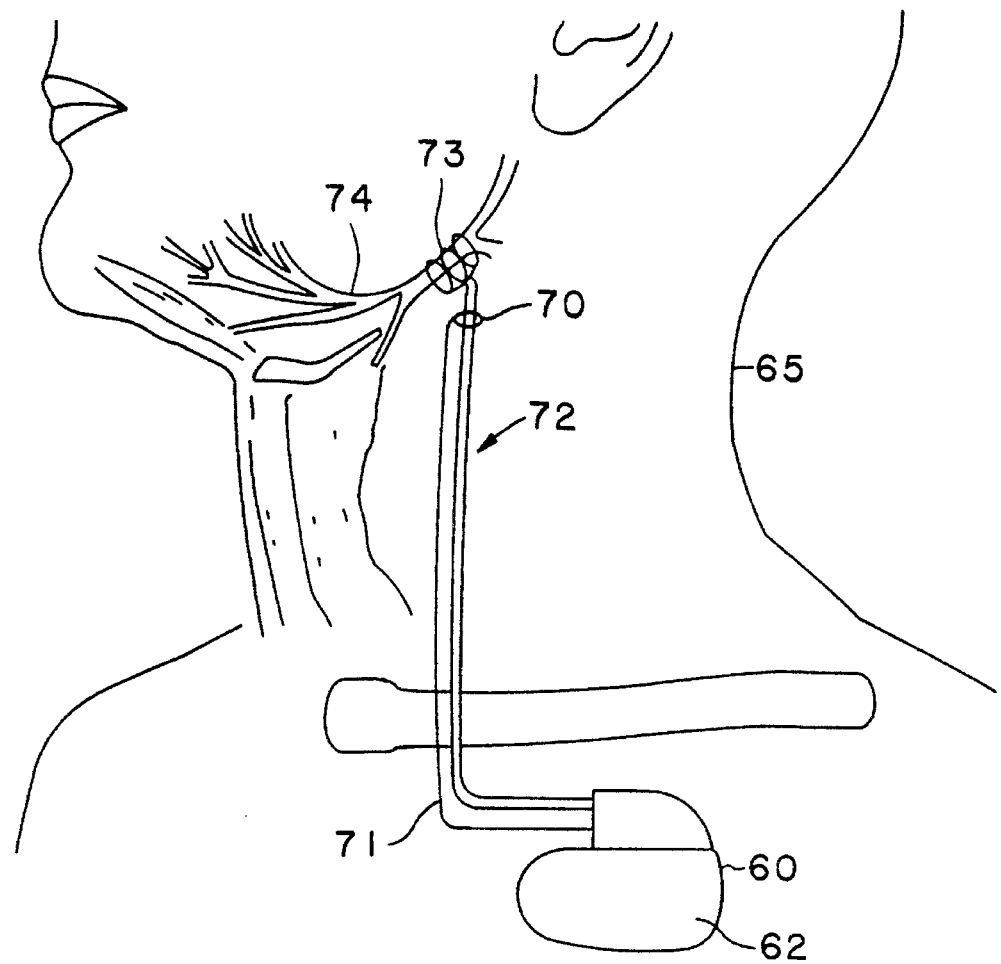
FIG. 5 is an embodiment of the invention using an implanted pulse generator and implanted impedance sensor.

A device operating substantially as described above can be implemented in a fully implantable stimulation system such as that shown in FIG. 5. In FIG. 5, an implantable pulse generator 60 (e.g. a Medtronic ITREL II Model 7424 modified to include an input from a respiratory sensor) can be implanted in a patient 65 with respiratory sensing between an impedance measuring electrode 70 and the case 62 of the pulse generator 60. The Medtronic ITREL II implantable IPG has advanced programmable features permitting mode changes by transcutaneous RF telemetry. The patient-controllable parameters of the device's operation can therefore be controlled by the patient through a small, hand-held telemetry device while the physician can preset additional operational parameters of the device through an external programmer. The impedance measuring electrode 70 is a ring electrode disposed about a lead 72 terminating in a stimulation electrode 73. Therefore, the surgical implantation of the stimulation electrode 73 and lead 72 also provides the implantation of one measuring electrode 70 of the impedance measuring circuit and an associated conductor 71. Inspiration-synchronous stimulation is provided from the pulse generator 60 through the lead 72 to the nerve electrode 73 around the hypoglossal nerve 74.

Figure 6:
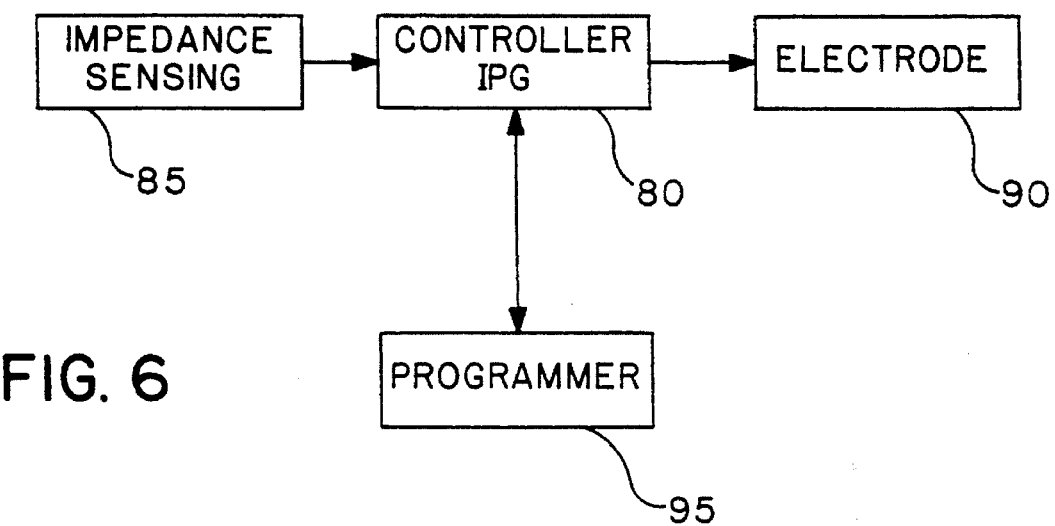
FIG. 6 is a block diagram of one embodiment of the apnea treatment device according to the present invention.

A block diagram of the principal elements of the device is shown in FIG. 6. That device includes a controller 80 which is capable of sensing the inspiratory phase and transmitting an electrical stimulus pulse to muscles of the upper airway. An impedance sensing circuit 85 sends respiratory waveform information to the controller 80 which sends stimulus pulses through an electrode 90 to stimulate the muscles of the patient. The electrode can be a Medtronic Model 3990 Half Cuff Nerve Electrode. A programmer 95 is capable of remote programming of controller 80 with various parameters in order to adapt the device to a particular patient. The device of FIG. 6 is therefore adapted to be programmed by the doctor and thereafter used each night by the patient to prevent the closure of the upper airway during the inspiratory phase of the respiration cycle. A programmer with basic on/off capabilities may also be provided to the patient in order to allow the patient to enable and disable the preprogrammed treatment. It will be apparent to those skilled in the art that the entire system must be made to be easy to use by the patient and since it is used without constant medical supervision, it must be able to safely adapt to many different operating conditions.

Figure 7:
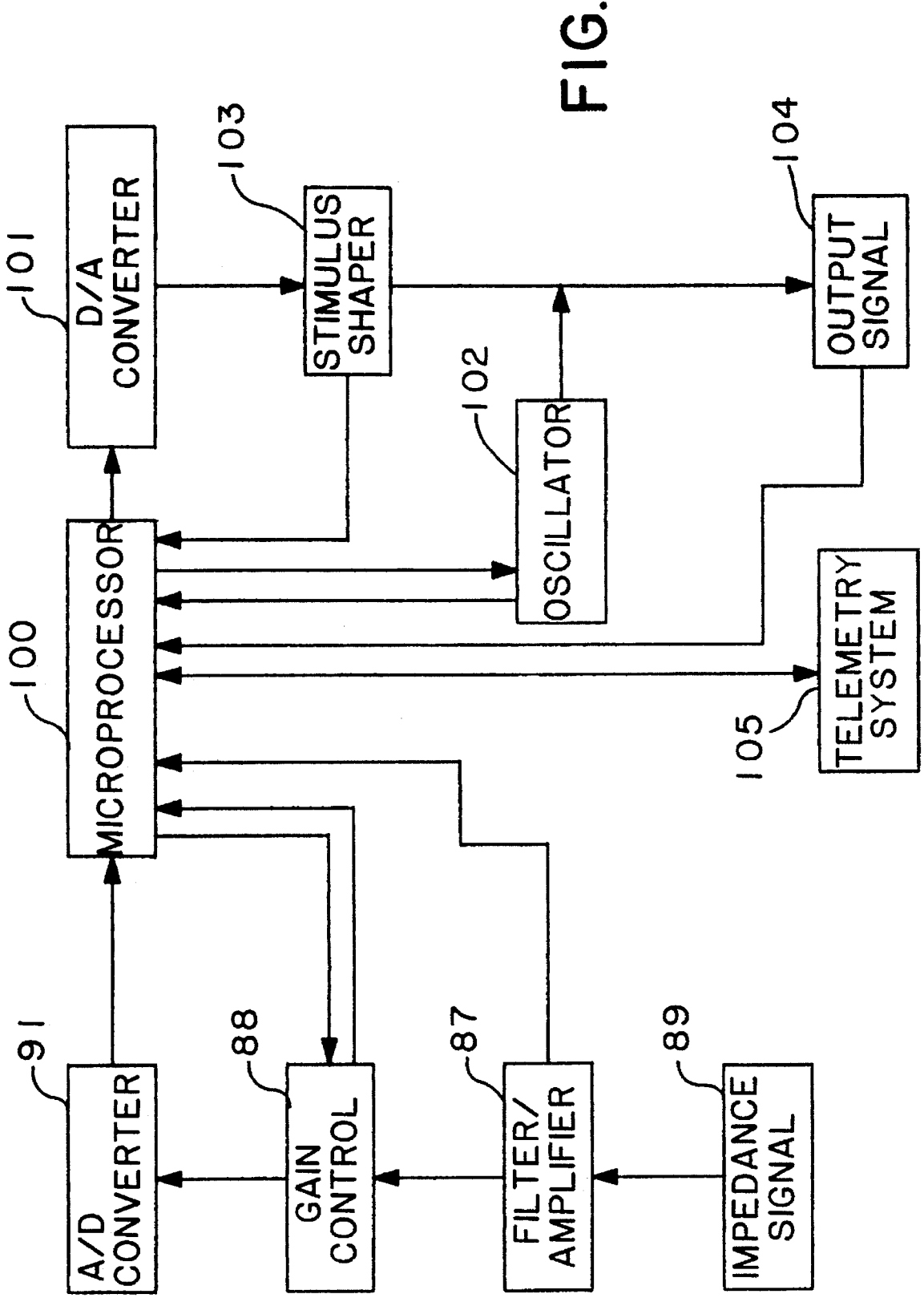
FIG. 7 is a block diagram of the upper airway transmitter/controller of FIG. 6. as it is applied to a patient.

FIG. 7 is a block diagram of the controller 80 of FIG. 6. A microprocessor 100 controls the principal operations of the controller 80. An impedance signal 89 from the impedance sensing circuit 85 is coupled to an amplifier/filter 87 which filters artifacts from the signal 89 and an automatic gain control 88 so that it is compatible with analog or digital signal processing devices such as an analog/digital converter 91. The microprocessor 100 provides data to the D/A converter 101 and the oscillator 102 which allows the stimulus waveform to be shaped by the stimulus shaper 103 into an output signal 104. A telemetry system 105 is used with an external programmer (not shown) to communicate with the microprocessor.

The impedance sensing circuit 85 includes lead 72, impedance measuring electrode 70 and IPG 60. The impedance sensing circuit 85 can measure cardiac impedance by outputting periodic biphasic current pulses on lead 72 to impedance measuring electrode 70, and then sensing the resulting voltages. The resulting voltages are sensed to generate a voltage waveform which reflects changes in impedance. The measured impedance changes will then be related to changes in frequency and magnitude of the patient's respiratory effort with the signal having peaks corresponding to the phases of the respiratory cycle in which the expiratory and inspiratory speeds reach their maximum values and will have a zero value when any respiratory dynamics is absent. At a predetermined period (e.g. every 20–100 ms), the microprocessor 100 samples the impedance waveform and determines a value indicating the magnitude of the change in the impedance waveform voltage since the last sample. Several components of the impedance sensing circuit 85 may be computational elements requiring externally supplied parameter values, such as are provided by a physician using an external programming device. Also, interactive protocols can be used in combination with these programmable parameters in order to optimize the response of the impedance sensing circuit 85. For example, a breathing protocol to provide an initial gain for the circuit can be used in which the patient is breathing normally at rest. Sensed impedance values during the test can be observed by the physician via the telemetry system and the initial gain for the circuit 85 programmed into a desired range.

The microprocessor 100 identifies the inspiration phase of the respiratory effort waveform from the digitized amplitude values from the impedance circuit 85 so that the system can supply a shaped stimulus burst for the duration of that phase at the electrode 90. The onset of inspiration is characterized as a sustained increase in slope of the impedance waveform greater than a preset threshold but less than a maximum slope value. Generally, an inspiratory turn point would be indicated by an increase in the impedance signal amplitude of between about 1.5X and 5X over two sample periods about 40 to 100 ms apart. The peak amplitude of the impedance signal indicates the end of inspiration and the onset of expiration. Generally, an inspiratory peak is detected if a negative slope for the impedance waveform is identified and sustained over three consecutive sample periods (i.e. over about 60 to 150 ms).

Alternatively, an analog derivative of the respiration impedance signal can be used to determine onset and offset of inspiration. In the analog mode of operation, the impedance circuit 85 output can be processed by the IPG to derive a time derivative of the measured impedance. A baseline value for the signal is then established by averaging about 10 consecutive voltage measurements. If the average is above the previous baseline by a predetermined voltage, then the baseline is reset to the average value. Once a valid baseline voltage has been established, a threshold voltage is established from the baseline voltage (e.g. baseline voltage minus a constant) that corresponds to the onset of inspiration. When the threshold voltage is achieved by the signal from the sensor, stimulation is enabled. In order to prevent false-positive indications of inspiratory onset, the signal voltage may be averaged and then compared with the threshold voltage. Inspiratory offset may be found in a similar manner by computing a second threshold voltage (i.e. a negative voltage characteristic of the expiratory phase of the respiratory cycle) and identifying the point at which the second threshold is achieved.

Figure 8A:
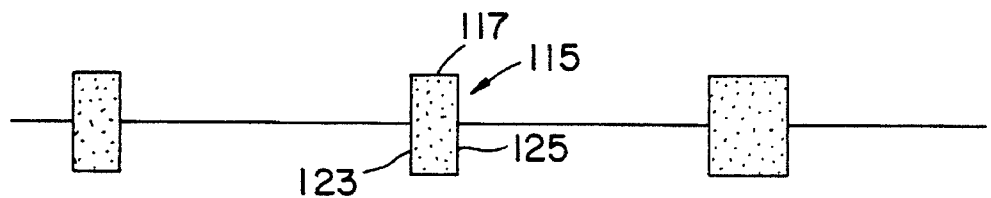
FIGS. 8a–c are waveforms showing the synchronization of stimulation from the upper airway transmitter of FIG. 6 (FIG. 8a) with the impedance respiratory waveform (FIG. 8b) and intratracheal pressure waveform (FIG. 8c).
Figure 8B:
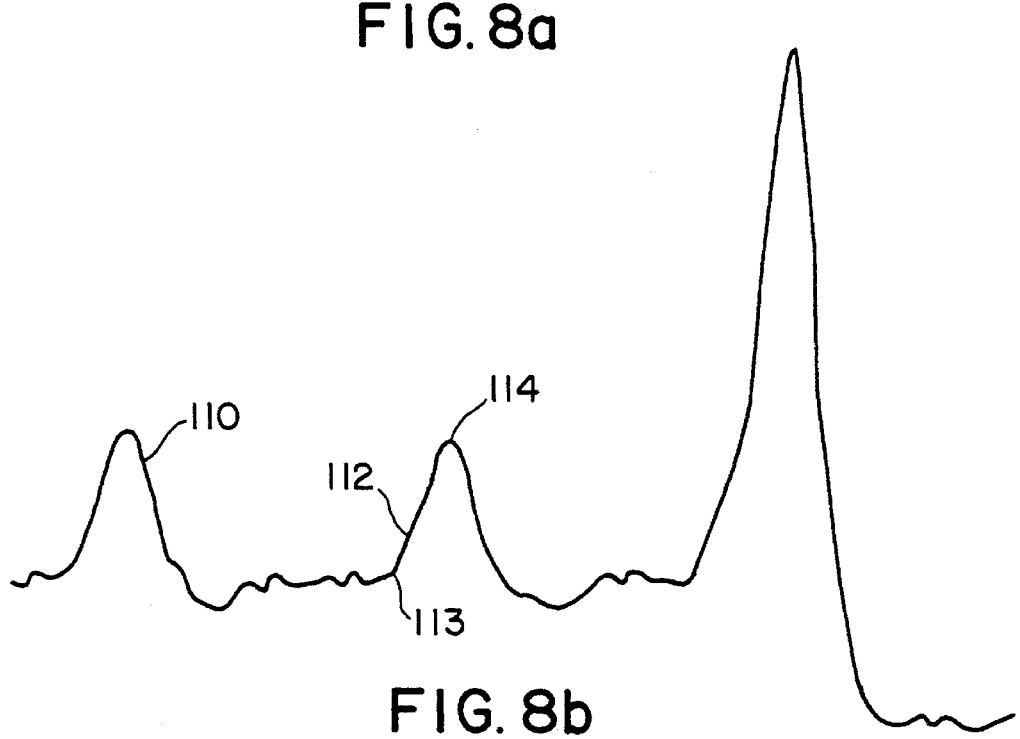
Figure 8C:
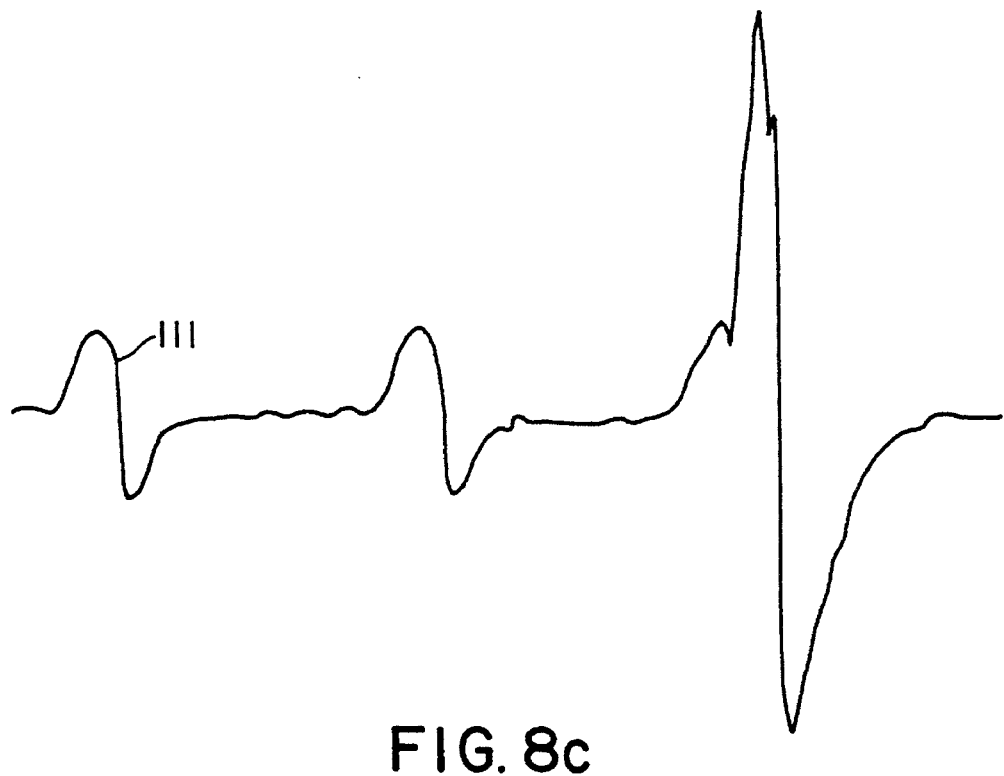

FIGS. 8a–c indicate the basic mode of operation for the system. The patient's respiratory signal 110 derived from implanted impedance sensing circuit is monitored and the inspiratory phase 112 of the signal 110 is identified from a waveform analysis which finds the turning point 113 and the inspiratory peak 114. This respiratory signal 110 can be seen to correspond closely with measured intratracheal pressure 111 in indicating the inspiratory phase of the respiratory cycle. The system then provides a bipolar stimulus burst to the appropriate upper airway musculature which is synchronized with the inspiratory phase 112. The stimulus burst is indicated as a stimulus window 115 which includes a peak amplitude 117 which is specifically set by the physician at a level required by the patient. A ramp gradually increasing the stimulus during a rise time and a ramp gradually decreasing stimulus during a fall time may also be provided if desired. Ideally, the stimulus would have a starting point 123 at the same time as the turning point 113 and continue to an end point 125 that is exactly at the inspiratory peak 114. However, due to the fact that there is always uncertainty as to whether the inspiratory peak 114 has been reached or whether the amplitude of the signal will continue to increase, the end point 125 for the stimulus window 115 may be delayed until the system clearly identifies the peak by seeing that the signal 110 is on a downward trend. Thus, the end point 125 may occur slightly after the inspiratory peak 114.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

I claim:

1. A method for treating upper airway obstruction in a patient by electrical stimulation of muscles of the upper airway by the steps of:
    (a) surgically implanting a pulse generator into the patient together with an impedance sensing circuit in a common case with the pulse generator;
    (b) surgically implanting a stimulation lead extending from the pulse generator to a nerve which activates at least one of the patient's upper airway muscles and at least two impedance measuring electrodes, at least one of said electrodes along said lead, said electrodes in electrical connection with the impedance sensing circuit such that the circuit provides a signal characteristic of thoracic impedance in the patient;
    (c) monitoring the impedance signal of the implanted impedance sensing circuit for at least one parameter characteristic of onset of inspiration of the patient;
    (d) detecting the onset of inspiration from the monitored parameter; and
    (e) applying the electrical stimulation synchronous with the onset of inspiration, the electrical stimulation applied at a level which restores patency in the airway.

2. The method of claim 1 wherein the step of monitoring the impedance signal includes the step of monitoring a slope of the impedance signal and the step of detecting the onset of inspiration includes the step of detecting a change in the monitored slope.

3. The method of claim 2 wherein the step of monitoring the slope includes the step of monitoring the slope over an interval of about 40 to 100 ms.

4. The method of claim 1 wherein the step of monitoring the impedance signal includes the step of monitoring an amplitude of the impedance signal and the step of detecting the onset of inspiration includes the step of detecting a threshold value for the amplitude of the impedance signal.

5. The method of claim 4 wherein the threshold value is determined by the steps of:
    (a) determining a baseline average value for the amplitude of the monitored signal;
    (b) determining a threshold value as a function of the baseline average value.

6. The method of claim 1 wherein the Step of surgically implanting a stimulation lead in electrical connection with an impedance sensing circuit such that the circuit provides a signal characteristic of thoracic impedance in the patient includes the step of digitizing the signal and the step of monitoring the impedance signal includes the step of monitoring the digital signal.

7. A medical device for treating upper airway obstruction in a patient by electrical stimulation of muscles of the upper airway comprising:
    (a) an implantable pulse generator;
    (b) an impedance sensing circuit in a common case with the pulse generator;
    (c) a stimulation lead adapted to extend from the pulse generator to a nerve which activates at least one of the patient's upper airway muscles;
    (d) at least two impedance measuring electrodes, at least one of said electrodes along said stimulation lead, said electrodes in electrical connection with the impedance sensing circuit such that the sensing circuit provides a signal characteristic of thoracic impedance in the patient;
    (e) means responsive to said impedance sensing circuit for monitoring the impedance signal of the implanted impedance sensing circuit for at least one parameter characteristic of the onset of inspiration of the patient;
    (f) means associated with said monitoring means for detecting the onset of inspiration; and
    (g) means responsive to said detecting means for applying the electrical stimulation synchronous with the onset of inspiration, the electrical stimulation applied at a level which restores patency in the airway.

8. The device of claim 7 wherein said monitoring means includes slope measuring means for measuring a slope of the impedance signal and said means associated with said monitoring means for detecting the onset of inspiration includes means responsive to said slope measuring means for detecting a change in the measured slope.

9. The device of claim 8 wherein the slope measuring means includes timing means and means for measuring the slope over an interval of about 40 to 100 ms.

10. The device of claim 7 wherein said detecting means includes threshold means responsive to said monitoring means for setting a threshold value for the onset of inspiration.

11. The device of claim 10 wherein the threshold means comprises:
    (a) means responsive to said monitoring means for determining a baseline average value for the monitored signal;
    (b) means responsive to said baseline determining means for determining the threshold value as a function of the baseline average value.

12. The device of claim 7 wherein the impedance sensing circuit also includes means for digitizing the impedance signal and the means for monitoring the impedance signal includes means for monitoring a digitized impedance signal.

\* \* \* \* \*